United States Patent [19]

Kondo et al.

[11] Patent Number: 4,950,686

[45] Date of Patent: Aug. 21, 1990

[54] ANTI-MYCOPLASMA AGENT

[75] Inventors: Eiji Kondo, Osaka; Yoshiyuki Hayashi, Shiga; Takao Konishi, Osaka; Teruo Hattori, Hyogo; Junichi Shoji, Osaka, all of Japan

[73] Assignee: Shionogi & Co., Ltd., Osaka, Japan

[21] Appl. No.: 86,583

[22] Filed: Aug. 18, 1987

[30] Foreign Application Priority Data

Aug. 21, 1986 [JP] Japan .............................. 61-196535

[51] Int. Cl.$^5$ .................... A61K 31/22; A61K 31/215
[52] U.S. Cl. ...................................... 514/546; 514/529
[58] Field of Search ................................ 514/546, 529

[56] References Cited

PUBLICATIONS

Chemical Abstracts 75:61884m (1971).
Chemical Abstracts, Formula Index, Jul. & Dec. 1971, p. 345F.

Primary Examiner—Jerome D. Goldberg
Attorney, Agent, or Firm—Wenderoth, Lind & Ponack

[57] ABSTRACT

An anti-mycoplasma agent comprising tropolone, its derivatives, represented by the formula:

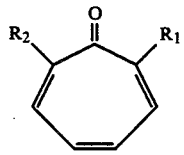

(wherein $R_1$ is hydroxy, aliphatic acyloxy, arylacyloxy, arysulfonyloxy, carboxyalkyloxy or its ester, benzoylalkyloxy, alkenyloxy, 1,3-dihydro-3-oxo-1-isobenzofuranyloxy, (2-oxo-5-methyl-1,3-dioxol-4-yl)methyloxy or thiocyanato and $R_2$ is hydrogen, halogen, hydroxy, alkyl or alkoxy) and their salts as an active ingredient, which has potent activity especially against tylosin-resistant mycoplasma both in vitro and in vivo and is effectively used in treating the diseases caused thereby.

1 Claim, No Drawings

ANTI-MYCOPLASMA AGENT

BACKGROUND OF THE INVENTION

1. Field of the Invention

This invention relates to an anti-mycoplasma agent comprising one or more of tropolone, its derivatives, which are represented by the following formula;

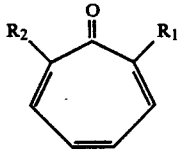

(where in $R_1$ is hydroxy, aliphatic acyloxy, arylacyloxy, arysulfonyloxy, carboxyalkyloxy or its ester, benzoylalkyloxy, alkenyloxy, 1,3-dihydro-3-oxo-1-isobenzofuranyloxy, (2-oxo-5-methyl-1,3-dioxol-4-yl)methyloxy or thiocyanato and $R_2$ is hydrogen, halogen, hydroxy, alkyl or alkoxy) and their salts. Specifically, this invention relates to an anti-mycoplasma agent comprising one or more of tropolone, its derivatives such as O-acetyltropolone, O-benzoyltropolone, O-(p-toluenesulfonyl)tropolone, O-(1-carboxyethyl)tropolone, O-(tert-butyloxycarbonylmethyl)tropolone, O-(pivaloyloxymethyl)tropolone, O-(1-ethoxycarbonylethyl)tropolone, O-(benzoylmethyl)tropolone, O-allyltropolone, O-(1,3-dihydro-3-oxo-1-isobenzofuranyl)tropolone, 7-bromotropolone, O-{(2-oxo-5-methyl-1,3-dioxol-4-yl)methyl}tropolone, 7-methoxytropolone, 7-hydroxytropolone, 7-methyltropolone, and 2-thiocyanatotropone, their complex with heavy metals such as iron, copper, cobalt and nickel, their salts with metals such as calcium, magnesium, zinc and sodium and their salts with organic bases such as ethanolamine, n-propylamine, lysine and arginine.

Further, this invention relates to a compound represented by the following formula;

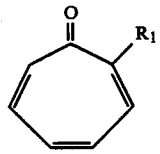

(wherein $R_1$ is 1-carboxyethyloxy, tert-butyloxycarbonylmethyloxy, 1-ethoxycarbonylethyloxy, 1,3-dihydro-3-oxo-1-isobenzofuranyloxy or (2-oxo-5-methyl-1,3-dioxol-4-yl)methyloxy).

2. Prior Art

Tropolone is a compound well known as bactericide and fungicide. It is prepared from tropone by the reaction with hydrazine and subsequent treatment of the resulting 2-aminotropone with an alkali or from cycloheptane-1,2-dione by the reaction with bromine and subsequent reduction of the resulting 3-bromotrope. It is also produced by some strain of the genus pseudomonas (J. Natural Products, vol. 43, No. 5, 592–594 (1980)). Its activity against bacteria and fungi has already been known (U.S. Pat. No. 3,448,155) but its activity against mycoplasma has not yet been found at all. With regard to derivatives of tropolone, acetyltropolone, benzoyltropolone and so on have already been synthesized (J. Amer. Chem. Soc., 73, 828 (1951)).

Now tylosin is mainly used for the therapy of animal diseases caused by mycoplasma. However, the emergence of tylosin-resistant mycoplasma is a present serious problem. Therefore, such anti-mycoplasma agent as effective against tylosin-resistant mycoplasma has been long desired.

SUMMARY

This invention provides an anti-mycoplasma agent containing one or more of tropolone, its derivatives represented by the formula;

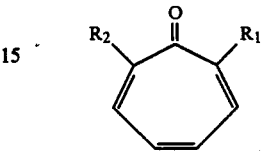

(wherein $R_1$ is hydroxy, aliphatic acyloxy, arylacyloxy, arysulfonyloxy, carboxyalkyloxy or its ester, benzoylalkyloxy, alkenyloxy, 1,3-dihydro-3-oxo-1-isobenzofuranyloxy, (2-oxo-5-methyl-1,3-dioxol-4-yl)methyloxy or thiocyanato and $R_2$ is hydrogen, halogen, hydroxy, alkyl or alkoxy) and their salts. The anti-mycoplasma agent of this invention has potent activity especially against tylosin-resistant mycoplasma both in vitro and in vivo and, therefore, this agent is effectively used in treating the diseases caused by tylosin-resistant mycoplasma.

DETAILED DESCRIPTION OF THE INVENTION

The present inventors have searched substances effective against tylosin-resistant mycoplasma and found that tropolone, its derivatives and their salts have a potent activity against mycoplasma, especially against tylosin-resistant mycoplasma.

This invention provides tropolone, various kinds of its derivatives and their salts as an active ingredient of an anti-mycoplasma agent. As its derivatives, compounds represented by the following formula are exemplified.

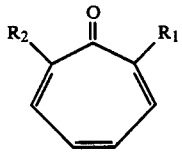

(wherein $R_1$ hydroxy, aliphatic acyloxy, arylacyloxy, arysulfonyloxy, carboxyalkyloxy or its ester, benzoylalkyloxy alkenyloxy, 1,3-dihydro-3-oxo-1-isobenzofuranyloxy, (2-oxo-5-methyl-1,3-dioxol-4-yl)methyloxy or thiocyanato and $R_2$ is hydrogen, halogen, hydroxy, alkyl or alkoxy). More specifically, O-acetyltropolone, O-benzoyltropolone, O-(p-toluenesulfonyl)tropolone, O-(1-carboxyethyl)tropolone, O-(tert-butyloxycarbonylmethyl)tropolone, O-(pivaloyloxymethyl)tropolone, O-(1-ethoxycarbonylethyl)tropolone, O-(benzoylmethyl)tropolone, O-allyltropolone, O-(1,3-dihydro-3-oxo-1-isobenzofuranyl)tropolone, 7-bromotropolone, O-{(2-oxo-5-methyl-1,3-dioxol-4-yl)methyl}tropolone, 7-methoxytropolone, 7-hydroxytropolone, 7-methyltropolone, 2-thiocyanatotropone and the like may be exemplified but this invention is not limited to these compounds since the compounds represented by the above formula are naturally expected to have anti-mycoplasma activity.

Further, this invention comprehends complexes and salts of the compounds of the above formula. For example, complexes with heavy metals such as iron, copper, cobalt and nickel, salts with metals such as calcium, magnesium, zinc and sodium, salts with organic bases such as ethanolamine, propylamine, lysine and arginine and ethers such as methyl ether may be exemplified.

Hereinafter these compounds may be referred to as a general term of them, that is, Tropolones.

Among the above Tropolones, compounds of the following formula;

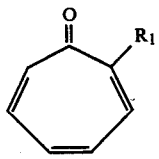

(wherein $R_1$ is 1-carboxyethyloxy, tert-butyloxycarbonylmethyloxy, 1-ethoxycarbonylethyloxy, 1,3-dihydro-3-oxo-1-isobenzofuranyloxy or (2-oxo-5-methyl-1,3-dioxol-4-yl)methyloxy) are novel and, therefore, this invention also provides these novel compounds.

In this invention tropolone on the market can be employed and, of course, tropolone synthesized according to the method described above can be employed, too. Other Tropolones as mentioned above can be prepared from tropolone as shown in the examples mentioned below.

An anti-mycoplasma agent containing one or more of Tropolones of this invention as active ingredients can be formulated alone or with suitable carriers usually applied to this kind of agent into various types of formulations such as powder, granules, liquid, suspension, premix, capsules, emulsion and tables, if necessary, with addition of disintegrator, lubricant, stabilizer, corrigent, coloring agent, preservative, aromatic and so on. As respects a carrier, various kinds of carriers usually used for a veterinary medicine can be applied to this agent; for example, water, gum arabic, lactose, sucrose, talc, colloidal silica, soybean cake, starch, yeast, wheat, defatted soybean, corn, wheat bran and other commercially available feed for a domestic animal.

The anti-mycoplasma agent of this invention can effectively be administered orally, intramuscularly, intravenously or subcutaneously. In a case of an oral administration the dose may be at 10–200 mg(active ingredient)/kg/day. Further, this agent may be dissolved in feed water or mixed with feed in a concentration of 100–1,000 ppm for effective administration.

As shown later in the following example, the anti-mycoplasma agent of this invention has potent activity especially against tylosin-resistant mycoplasma both in vitro and in vivo and, therefore, this agent is effectively used in treating the diseases caused by tylosin-resistant mycoplasma.

EXAMPLE

Example 1

(1) Tropolone iron complex

To a solution of tropolone (103 mg) in chloroform is added a solution of ferric chloride (137 mg) in ethanol. After concentration under reduced pressure, the residue is dissolved in chloroform. A small amount of the insoluble material is removed by filtration and the solvent is evaporated under reduced pressure. The resulting precipitate is recrystallized from chloroform-methanol to give 85 mg of tropolone iron complex as brown plates.

(2) Tropolone copper complex

To a solution of tropolone (244 mg) in water is added a suspension of copper (II) hydroxide (98 mg) in water. The mixture is heated at 80° C. and methanol-chloroform is added thereto until the mixture becomes homogeneous. The solution is concentrated under reduced pressure. The depositing green crystals are collected by filtration and dissolved in hot chloroform. After removing impurities by filtration, to the filtrate is added methanol. The solution is cooled with ice. The precipitating green needles are recovered by filtration to give tropolone copper complex (203 mg).

(3) Tropolone cobalt complex

To a solution of tropolone (244 mg) in methanol is added a solution of cobalt (II) chloride (129 mg) in water and then sodium acetate (164 mg). The precipitate is recovered by filtration and recrystallized from ethanol-ethyl acetate to give 206 mg of tropolone cobalt complex as brown powder.

(4) Tropolone nickel complex

Tropolone (244 mg) is treated with nickel chloride hexahydrate (237 mg) in the same manner as that in the case of cobalt complex to give 287 mg of tropolone nickel complex as light green needles.

(5) Tropolone calcium salt

A solution of tropolone (976 mg) in methanol is added to a solution of calcium hydroxide (296 mg) dissolved in hot water (30 ml) and stirred at 90° C. for 15 min. After allowed to stand and then cooled with ice, the precipitate is recovered by filtration, washed with water and dried to give tropolone calcium salt (119 mg).

m.p.>260° C. (gradually decomposing over 260° C.)

Anal. Calcd. for $(C_7H_5O_2)_2.Ca.H_2O$: C;56.84 H;3.92; Found: C;57.16 H;3.97.

(6) Tropolone magnesium salt

A solution of tropolone (122 mg) in methanol is added to a solution of magnesium hydroxide (29 mg) in methanol-water (1:1, 30 ml). The mixture is stirred at 80° C. for 10 min. After removing a small amount of impurities by filtration, the filtrate is concentrated under reduced pressure to remove methanol. After lyophilization, the resulting powder is washed with ether and dried to give tropolone magnesium salt (144 mg).

m.p.>290° C. (not melting at 290° C.)

Anal. Calcd. for $(C_7H_5O_2)_2.Mg.\frac{1}{4}H_2O$: C;62.03 H;3.90; Found: C;62.46 H;3.97.

(7) Tropolone zinc salt

Tropolone (122 mg) is treated with zinc hydoxide (50 mg) in the same manner as that in the case of magnesium salt to give tropolone zinc salt (118 mg).

m.p.>290° C.

Anal. Calcd. for $(C_7H_5O_2)_2.Zn.H_2O$: C;51.64 H;3.71; Found: C;51.79 H;3.22.

(8) Tropolone sodium salt

To a solution of tropolone (616 mg) in water is added 1N sodium hydroxide (5 ml). After lyophilization the powder is washed with ether and dried to give tropolone sodium salt (690 mg).

m.p.>290° C.

Anal. Calcd. for $C_7H_5O_2Na$: C;58.34 H;3.50; Found: C;58.44 H;3.77.

(9) Tropolone ethanolamine salt

To a solution of tropolone (735 mg) in methanol is added a solution of ethanolamine (420 mg) in methanol. After concentration under reduced pressure, the resulting residue is recrystallized from acetone to give 946 mg of tropolone ethanolamine salt as light yellow crystals.

m.p. 113°–115° C.

Anal. Calcd. for $C_9H_{13}NO_3$: C;59.00 H;7.15 N;7.65; Found: C;58.66 H;7.04 N;7.65.

(10) Tropolone n-propylamine salt

To a solution of tropolone (246 mg) in methanol is added a solution of n-propylamine (126 mg) in methanol. After concentration under reduced pressure, the resulting residue is recrystallized from ethanol-ether-petroleum ether to give 183 mg of tropolone n-propylamine salt as colorless needles.

m.p. 94°–96° C.

Anal. Calcd. for $C_{10}H_{15}NO_2 \cdot \frac{1}{4}H_2O$: C;64.66 H;8.41 N;7.54; Found: C;64.42 H;8.00 N;7.43.

(11) Tropolone L-lysine salt

To a solution of tropolone (244 mg) in water is added a solution of L-lysine (292 mg) in water. After lyophilization, the resulting residue is recrystallized from water-ethanol to give 473 mg of tropolone L-lysine salt as light yellow crystals.

m.p. >215° C. (gradually decomposing over 215° C., not showing clear m.p.)

Anal. Calcd. for $C_{13}H_{20}N_2O_4$: C;58.19 H;7.51 N;10.44; Found: C;57.82 H;7.42 N;10.40.

(12) Tropolone L-arginine salt

To a solution of tropolone (244 mg) in water is added a solution of L-arginine (348 mg) in water. After lyophilization, the resulting residue is washed with a mixture of ethanol and ether and dried to give 606 mg of tropolone L-arginine salt as light yellow powder.

m.p. (gradually decomposing over 85° C., not showing clear m.p.)

Anal. Calcd. for $C_{13}H_{20}N_4O_4 \cdot \frac{1}{2}H_2O$: C;51.13 H;6.93 N;18.35; Found: C;50.98 H;7.13 N;17.95.

(13) O-Acetyltropolone

To a solution of tropolone (1,460 mg) dissolved in pyridine (30 ml) is added acetic anhydride (2.0 ml) under ice-cooling. The mixture is stirred at 0° C. for 5 hr. After allowed to stand at room temperature for 16 hr, the mixture is diluted with water under ice-cooling, adjusting to pH 3.0 with 6N hydrochloric acid and extracted with chloroform. The chloroform layer is washed with successive, 1M sodium carbonate, water and saturated brine and dried with anhydrous sodium sulfate. The sodium sulfate is removed by filtration and the solvent is evaporated under reduced pressure. The resulting residue is recrystallized from cyclohexane to give O-acetyltropolone (978 mg) as crystals.

m.p. 80° C.

Anal. Calcd. for $C_9H_8O_3$: C;65.85 H;4.91; Found: C;65.95 H;5.05.

(14) O-Benzoyltropolone

To a solution of tropolone (366 mg) dissolved in pyridine (5 ml) is added dropwise benzoyl chloride (0.6 ml). The mixture is stirred at room temperature for 3 hr and diluted with water. After cooling with ice, the precipitate is recovered by filtration and recrystallized from ethanol to give O-benzoyltropolone (586 mg) as crystals.

m.p. 129°–130° C.

Anal. Calcd. for $C_{14}H_{10}O_3$: C;74.33 H;4.45; Found: C;73.83 H;4.61.

(15) 2-Thiocyanatotropone

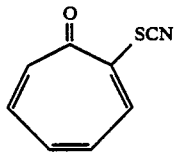

To a solution of tropolone (1,680 mg) dissolved in benzene (36 ml) is added thionyl chloride (1.12 ml). The mixture is stirred for 1.5 hr with refluxing. After concentrating the reaction mixture under reduced pressure, the resulting residue is purified by silica gel chromatography and recrystallized from cyclohexane to give 1.08 g of 2-chlorotropone as yellow needles. To a solution of the 2-chlorotropone (75 mg) dissolved in dimethylformamide (4 ml) is added potassium thiocyanate (270 mg). The mixture is stirred at 110° C. for 26 hr. To the reaction mixture is added water (50 ml), followed by cooling with ice. The resulting precipitate is recovered by filtration, purified by silica gel chromatography and recrystallized from ethanol to give 59 mg of 2-thiocyanatotropone as light brown needles.

m.p. 161°–163° C.

Anal. Calcd. for $C_8H_5NOS$: C;58.88 H;3.09 N;8.59 S;19.65; Found: C;59.01 H;3.44 N;8.55 S;19.40.

(13) O-(p-Toluensulfonyl)tropolone

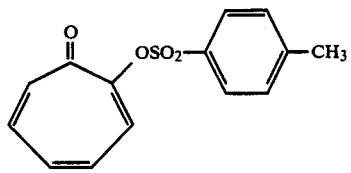

To a solution of tropolone (0.61 g) dissolved in N,N-dimethylformamide (20 ml) is added 60% sodium hydride (210 mg). The mixture is stirred at 0° C. for 30 min. To the mixture is added p-toluenesulfonyl chloride (1.14 g). The mixture is stirred for 4 hr on an oil bath (75° C.) and extracted with ethyl acetate. The ethyl acetate layer is washed with water and then with saturated brine and dried with anhydrous sodium sulfate to give crude crystals (885 mg), which are further purified by silica gel chromatography and recrystallized from benzene to give 0.37 g of O-(p-toluensulfonyl)tropolone as colorless prisms.

m.p. 159°–160° C.

Anal. Calcd. for $C_{14}H_{12}O_4S$: C;60.86 H;4.38 S;11.60; Found: C;60.93 H;4.24 S;11.48.

(17) O-(1-Carboxyethyl)tropolone

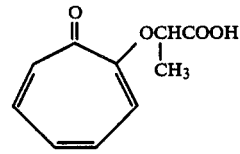

To 0.50 g of O-(1-ethoxycarbonylethyl)tropolone (20) is added 5% sodium hydroxide at room temperature. After stirring for 10 min, 5% hydrochloric acid is added to the reaction mixture until it becomes pH 1. Then, the mixture is extracted with ethyl acetate. The ethyl acetate layer is dried with anhydrous sodium sulfate and evaporated to give crude crystals (0.35 g). This is recrystallized from chloroform/n-hexane to give 0.22 g of O-(1-carboxyethyl)tropolone as light yellow prisms.

m.p. 145°–146° C.

Anal. Calcd. for C₁₀H₁₀O₄: C;61.85 H;5.19; Found: C;61.60 H;5.21.

(18) O-(tert-Butyloxycarbonylmethyl)tropolone

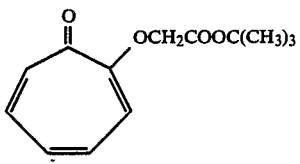

To a solution of tropolone (0.61 g) dissolved in N,N-dimethylformamide (20 ml) is added 60% sodium hydride (0.24 g). After stirring at 0° C. for 30 min., tert-butyl chloroacetate (1.14 g) is added dropwise at 0° C. to the reaction mixture. After stirring on an oil bath (50° C.) for 1 hr and then refluxing at 150° C. for 1 hr, the reaction mixture is extracted with dichloromethane. The dichloromethane layer is washed with water, dried with anhydrous sodium sulfate, purified by silica gel chromatography and recrystallized from cyclohexane to give 0.39 g of O-(tert-butyloxycarbonylmethyl)-tropolone as light yellow prisms.

m.p. 90°–91° C.

Anal. Calcd. for C₁₃H₁₆O: C;66.09 H;6.83; Found: C;66.17 H;6.72.

(19) O-(pivaloyloxymethyl)tropolone

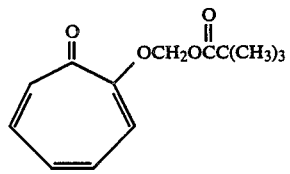

To a solution of tropolone (2.44 g) dissolved in N,N-dimethylformamide (20 ml) is added 60% sodium hydride (1.03 g). After stirring at 0° C. for 30 min, chloromethyl pivalate (4.0 g) is added dropwise to the reaction mixture at 0° C. The mixture is stirred on an oil bath (135° C.) for 3 hr and extracted with ether. The organic layer is washed with water, dried with sodium sulfate and evaporated to give an oily substance, which is purified by silica gel chromatography and evaporated to give crude crystals (1.97 g). This is recrystallized from cyclohexane to give colorless neddles (1.50 g).

m.p. 57°–58° C.

Anal. Calcd. for C₁₃H₁₆O₄: C;66.09 H;6.83; Found: C;66.04 H;6.81.

(20) O-(1-Ethoxycarbonylethyl)tropolone

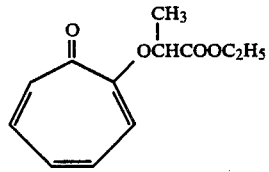

To a solution of tropolone (3.75 g) dissolved in N,N-dimethylformamide (40 ml) is added 60% sodium hydride (1.44 g). After stirring at 0° C. for 30 min, ethyl α-bromopropionate (6.52 g) is added dropwise to the reaction mixture at room temperature. After stirring on an oil bath (75° C.) for 21 hr, the reaction mixture is extracted with dichloromethane. The dichloromethane layer is washed with water, dried, evaporated, purified by silica gel chromatography and recrystallized from cyclohexane to give 1.02 g of O-(1-ethoxycarbonyle-thyl)tropolone as colorless prisms.

m.p. 66°–67° C.

Anal. Calcd. for C₁₂H₁₄O₄: C;64.85 H;6.35; Found: C;64.72 H;6.40.

(21) O-(Benzoylmethyl)tropolone

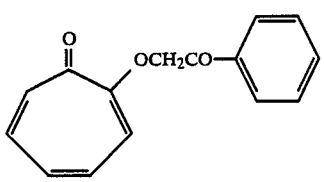

To a solution of tropolone (0.69 g) dissolved in dioxane (20 ml) is added silver oxide (1.17 g). After stirring at room temperature for 30 min, 2-bromoacetophenone (1.12 g) is added to the mixture, followed by stirring at room temperature for 7 days. After the insoluble materials in the reaction mixture are removed by filtration, the filtrate is extracted with dichloromethane. The dichloromethane layer is washed with water, dried with sodium sulfate and evaporated to give an oily substance. This is purified by silica gel chromatography and recrystallized from toluene/n-hexane to give 59 mg of O-(benzoylmethyl)tropolone as colorless needles.

m.p. 130°–131° C.

Anal. Calcd. for C₁₅H₁₂O₃: C;74.99 H;5.04; Found: C;75.11 H;5.16.

(22) O-Allyltropolone

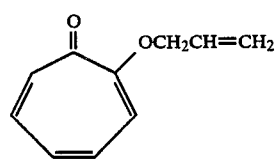

To a solution of tropolone (0.61 g) dissolved in dioxane (20 ml) is added silver oxide (1.16 g). After stirring at room temperature for 30 min, allyl bromide (1.10 g) is added to the mixture and stirred at room temperature for 24 hr. After removing the insoluble substances in the reaction mixture by filtration, the filtrate is extracted with dichloromethane. The dichloromethane layer is washed with water, dried with anhydrous sodium sulfate and evaporated to give an oily substance. This is purified by silica gel chromatography to give 0.37 g of O-allyltropolone as an oily substance.

$n_D^{23.6} = 1.3765$

Anal. Calcd. for C₁₀H₁₀O₂·⅛H₂O: C;73.04 H;6.28; Found: C;73.07 H;6.35.

(23) O-(1,3-Dihydro-3-oxo-1-isobenzofuranyl)tropolone

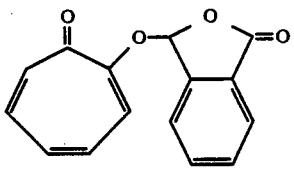

To a solution of tropolone (1.22 g) dissolved in N,N-dimethylformamide (20 ml) is added 60% sodium hydride (0.48 g). After stirring at 0° C. for 30 min, 3-chlorophthalide (2.00 g) is mixed with the reaction mixture. The mixture is stirred at room temperature for 30 min and then on an oil bath (110° C.) for 3 hr. The mixture is extracted with diethyl ether. The ether layer is washed with water, dried with anhydrous sodium sulfate and evaporated to give crude light yellow crystals. This is purified by silica gel chromatography and recrystallized from cyclohexane-ethyl acetate to give 0.46 g of O-(1,3-dihydro-3-oxo-1-isobenzofuranyl)-tropolone as light yellow crystals.

m.p. 154°–155° C.

Anal. Calcd. for $C_{15}H_{10}O_4$: C;70.86 H;3.97; Found: C;70.90 H;4.20.

(24) 7-Bromotropolone

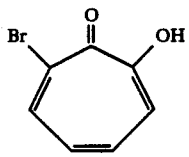

To a solution of cycloheptanone (6.80 g) dissolved in ethanol (14 ml) is added selenium dioxide (6,660 mg). After refluxing on an oil bath (88° C.) for 4 hr, insoluble materials are removed by filtration. The resulting mixture is distilled under reduced pressure (110° C./15 mm Hg) for purification to give 5.12 g of 1,2-cycloheptadione as an yellow oily substance. To this 1,2-cycloheptadione (5.05 g) are added acetic acid (2 ml) and acetate anhydride (0.2 ml). After stirring at room temperature for 18 hr and then cooling to 0° C., a solution of bromine (4.1 ml) and acetic acid (4 ml) is gradually added dropwise thereto. This mixture is allowed to react at room temperature for 3 days. The resulting precipitate is recovered by filtration. A suspension of this precipitate in water is adjusted to pH 3–4 with 20% sodium hydroxide. The precipitate is recovered by filtration to give a crude crystal of 7-bromotropolone. This is recrystallized from cyclohexane to give 7-bromotropolone as yellow needles.

m.p. 104°–105° C.

Anal. Calcd. for $C_7H_5BrO_2$: C;41.82 H;2.51 Br;39.75; Found: C;41.55 H;2.65 Br;39.97.

(25) O-{(2-Oxo-5-methyl-1,3-dioxol-4-yl)methyl}tropolone

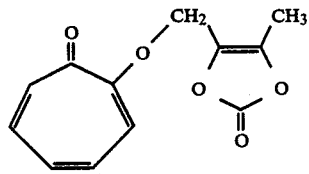

To a solution of tropolone (0.61 g) dissolved in N,N-dimethylformamide (20 ml) is added 60% sodium hydride (0.24 g). After stirring at 0° C. for 30 min, 5-bromomethyl-4-methyl-2-oxo-1,3-dioxolene (1.20 g) is added dropwise to the reaction mixture. The mixture is stirred at room temperature for 40 min, then on an oil bath (65° C.) for 20 min, and further at room temperature for 5 hr. This reaction mixture is extracted with dichloromethane and the extract is washed with water, dried with anhydrous sodium sulfate and evaporated to give an crude crystals (1.39 g). This is purified by silica gel chromatography and recrystallized from toluene to give 0.31 g of O-{(2-oxo-5-methyl-1,3-dioxol-4-yl)-methyl}tropolone as colorless prisms.

m.p. 150°–151° C.

Anal. Calcd. for $C_{12}H_{10}O_5$: C;61.54 H;4.30; Found: C;61.64 H;4.26.

(26) 7-Methoxytropolone

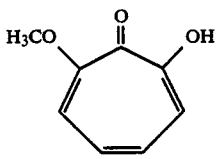

To 7-bromotropolone (1.01 g) are added copper oxide (0.20 g), pyridine (0.6 ml), methanol (20 ml) and 28% sodium methylate (3.38 g). The mixture is sealed in a tube, which is heated in an oil bath (145°–150° C.) for 20 hr. After cooling and then opening the tube, the insoluble substance is removed by filtration. After evaporation under reduced pressure, water (50 ml) is added to the resultant. The mixture is adjusted to pH 1 with 5% hydrochloric acid, extracted with dichloromethane, dried and evaporated to give crude crystals (1.43 g). This is treated with active carbon and recrystallized from cyclohexane to give 0.31 g of 7-methoxytropolone as light yellow needles.

m.p. 106°–108° C.

Anal. Calcd. for $C_8H_8O_3$: C;63.15 H;5.30; Found: C;63.05 H;5.44.

(27) 7-Hydroxytropolone

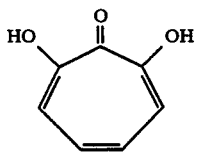

To a solution of 7-bromotropolone (1.96 g) dissolved in acetic acid (20 ml) are added 36% hydrochloric acid (20 ml) and water (8 ml). The mixture is sealed in a tube and allowed to react in a heater (170°–180° C.) for 12 hr. After cooling and then opening the tube, the insoluble substance is removed by filtration. The filtrate is extracted with diethyl ether for 10 hr. Then, the ether layer is evaporated to give crude crystals (0.91 g). This is treated with active carbon and recrystallized from toluene to give 0.19 g of 7-hydroxytropolone 1/10 hydrate as yellow needles.

m.p. 122°–123° C.

Anal. Calcd. for $C_7H_6O_3 \cdot 1/10\ H_2O$: C;60.08 H;4.47; Found: C;60.22 H;4.35.

(28) 7-Methyltropolone

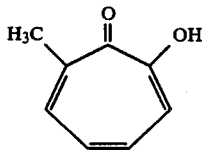

To 7-hydroxymethyltropolone (0.39 g) are added iodine (0.58 g), red phosphorus (0.58 g), acetic acid (12 ml) and water (1.2 ml). The mixture is refluxed on an oil bath (115°–120° C.) for 1 hr. After the reaction completion, the insoluble substance is removed by filtration. To the filtrate is added water (120 ml). The mixture is adjusted to pH 4 with 2N sodium hydroxide. The free iodine is treated with 10% sodium sulfite. After extraction with chloroform, the organic layer is dried with anhydrous sodium sulfate and evaporated to give crude crystals (0.33 g). This is purified by silica gel chromatography and recrystallized from n-hexane to give 97 mg of colorless scales.

m.p. 48°–49° C.

Anal. Calcd. for $C_8H_8O_2$: C;70.57 H;5.92; Found: C;70.32 H;6.00.

In the following examples each compound may be referred to as the number given in the above example.

Example 2

(1) In 1,000 ml of water is dissolved 500, 400, 200, 100 or 50 mg of tropolone to prepare 0.05, 0.04, 0.02, 0.01 or 0.005% aqueous solution of tropolone for administration by feed water.

(2) With 1,000 g of feed is mixed 500, 400, 200, 100 or 50 mg of tropolone to prepare the feed containing 500, 400, 200, 100 or 50 ppm of tropolone.

(3) In 25 ml of each of the following solutions a to h is dissolved 500, 250 or 125 mg of each of Tropolones to give 20, 10 or 5 mg/ml of Tropolones-preparation for oral administration.

a: 3% gum arabic
b: 5% gum arabic
c: 3% gum arabic + 20 mg/ml sodium citrate
d: 20% ethanol
e: 20 mg/ml sodium citrate
f: 10 g of sodium carboxymethylcellulose, 8 g of Tween 80, 18 g of benzyl alcohol and 18 g of sodium chloride in 2 L of distilled water
g: 20% DMSO
h: distilled water Test (1) Anti-mycoplasma activity test in vitro MIC values of each of Tropolones were measured on the following strains according to the following method.

(a) *Mycoplasma gallisepticum*

Strain:
S6 (standard strain)
T-7-T (wild strain, tylosin-resistant)
MR-1 (wild strain, tylosin-resistant)

Medium: Chick PPLO broth supplemented with 20% equine serum (Eiken Kagaku Co., Ltd.)

Method: Broth dilution method

Inoculum: Culture incubated at 37° C. for 24–48 hr which is diluted with broth to $10^6$ CCU/ml immediately before the use.

To 1.6 ml of the broth is added 0.2 ml of an agent which has been subjected to 2-fold dilution and then added 0.2 ml of inoculum, which is incubated at 37° C. for 7 days. A concentration of a test group whose color does not change (not becoming yellow) is regarded as MIC value when color of the control inoculum to which no agent is added changes.

(b) *Mycoplasma hyopneumoniae*

Strain: ST-11 (standard strain)

Medium: 850 ml of Hanks' solution supplemented with 0.5% lactoalbumin, 50 ml of 25% yeast, 100 ml of equine serum and 4–6 ml of 0.5% phenol red (pH 7.4–7.6)

Method: Broth dilution method

Inoculum: Culture which is incubated for 3–4 days and diluted 10 times with the broth if color of the broth becomes yellow then. If it needs over 4 days until color of the broth becomes yellow, it is further subcultured. This is diluted 10 times with the broth to give inoculum.

Assay is done in the same manner as in the above (a). The result is shown in Table 1.

TABLE 1

| Compound (Number) | MIC (μg/ml) Mg | | | Mh |
|---|---|---|---|---|
| | S6 | T-7-T | MR-1 | ST-11 |
| Tropolone | 0.2 | 0.39 | 0.39 | 0.78 |
| 1 | 0.78 | 0.78 | 0.56 | 0.39 |
| 2 | 3.13 | 3.13 | 3.13 | 0.78 |
| 3 | 1.56 | 1.56 | 3.13 | 0.78 |
| 4 | 1.56 | 3.13 | 3.13 | 0.78 |
| 5 | 3.13 | ND | 1.56 | ND |
| 6 | 1.56 | 1.56 | 1.56 | 0.78 |
| 7 | 1.56 | 3.13 | 3.13 | 0.78 |
| 8 | 1.56 | 1.56 | 1.56 | 0.78 |
| 9 | 3.13 | ND | 3.13 | ND |
| 10 | 3.13 | 3.13 | 3.13 | 0.78 |
| 11 | 0.39 | 0.78 | 0.78 | 0.78 |
| 12 | 3.13 | 3.13 | 3.13 | 1.56 |
| 13 | 0.39 | 0.78 | 0.78 | ND |
| 14 | 6.25 | 6.25 | 6.25 | 0.78 |
| 15 | 6.25 | 6.25 | 12.5 | 0.39 |
| 16 | 3.13 | ND | ND | 6.25 |
| 17 | 25.0< | ND | ND | 25.0< |
| 18 | 25.0< | ND | ND | 25.0< |
| 19 | 0.39 | 0.78 | 1.56 | 0.1 |
| 20 | 25.0< | 25.0< | ND | 25.0< |
| 21 | 0.78 | ND | ND | 0.2 |
| 22 | 25.0< | ND | ND | 25.0 |
| 23 | 0.39 | 0.78 | 0.78 | 0.39 |
| 24 | 0.39 | 0.78 | 1.56 | 0.2 |
| 25 | 0.39 | 0.39 | 0.39 | 0.2 |
| 26 | 6.25 | 12.5 | 6.25 | 3.13 |
| 27 | 12.5 | 12.5 | 12.5 | 12.5 |
| 28 | 0.1 | 0.39 | 0.2 | 0.1 |

Mg: *Mycoplasma gallisepticum*
Mh: *Mycoplasma hyopneum*
ND: No Data (2) Test of Effectiveness *Mycoplasma gallisepticum* air-sac infection method Strain:
S6 (standard strain)
T-7-T (wild strain, tylosin-resistant)
MR-1 (wild strain, tylosin-resistant)

Inoculation: To the right air-sac of 9 days old SPF chicken (a white leghorn) which has abstained from water and feed one day before is inoculated 0.20–0.25 ml/chicken of fresh mycoplasma culture incubated for 24–48 hr and diluted with broth (usually 100 times). The concentration in Table 2 is shown in a unit of mg/ml.

Medium: Chick PPLO broth supplemented with 15% equine serum (Eiken Kagaku Co., Ltd.)

Administration: A compound of this invention dissolved or suspended in the following solution is orally and forcibly administered once by a cannula immediately after the infection.

a: 3% gum arabic
b: 5% gum arabic
c: 20% ethanol
DW: distilled water

Anatomization and Isolation of Microorganism: The chickens are anatomized 5 days after the infection, and the right and left air sacs are investigated whether they are attacked with a disease or not. The change caused by the disease is represented in four degrees; —: no change, +: slight, ++: medium and +++: serious. Microorganism is isolated from the right and left air-sacs and the trachea by using a sterilized applicator.

Judgement: Judgement is done through an index of an air-sac disease and an index of a microorganism-isolation.

Index of an air-sac-disease: First, indexes in the right and left air-sacs are separately calculated according to the following formula;

{degree of disease (0–3)×chickens}/anatomized chickens and the index is calculated by the following formula;

(index of right air-sac)×1+(index of left air-sac)×2 range: 0–9.0
Index of a microorganism isolation:

$(P \times 1 + Q \times 2 + R \times 3)/S$

P: chickens from the right air-sac of which microorganism is isolated,
Q: chickens from the trachea of which microorganism is isolated,
R: chickens from the left air-sac of which microorganism is isolated, and
S: chickens investigated.
range: 0–6.0

The result is shown in Table 2.

TABLE 2

| Strain | Compound (Compound No.) | Administration Dose | Route | Conc | Sol. | Inoculum size | Tested Chickens |
|---|---|---|---|---|---|---|---|
| S6 | tropolone | 100 mg/kg × once | Oral | 10 | b | $6.3 \times 10^4$ | 5 |
|  | tropolone | 50 mg/kg × once | Oral | 5 | b | $6.3 \times 10^4$ | 5 |
|  | 5 | 200 mg/kg × once | Oral | 20 | c | $6.3 \times 10^4$ | 5 |
|  | 9 | 200 mg/kg × once | Oral | 20 | c | $6.3 \times 10^4$ | 5 |
|  | 13 | 200 mg/kg × once | Oral | 20 | c | $6.3 \times 10^4$ | 5 |
|  | Control | — | — | — | — | $6.3 \times 10^4$ | 5 |
|  | tropolone | 200 mg/kg × once | Oral | 20 | a | $3.1 \times 10^5$ | 5 |
|  | tropolone | 200 mg/kg × once | Oral | 20 | c | $3.1 \times 10^5$ | 5 |
|  | Control | — | — | — | — | $3.1 \times 10^5$ | 5 |
|  | 11 | 200 mg/kg × once | Oral | 20 | b | $1.18 \times 10^6$ | 5 |
|  | 12 | 200 mg/kg × once | Oral | 20 | b | $1.18 \times 10^6$ | 5 |
|  | Control | — | — | — | — | $1.18 \times 10^6$ | 5 |
|  | tropolone | 100 mg/kg × once | Oral | 10 | b | $1.2 \times 10^6$ | 8 |
|  | 13 | 100 mg/kg × once | Oral | 10 | b | $1.2 \times 10^6$ | 8 |
|  | 11 | 100 mg/kg × once | Oral | 10 | b | $1.2 \times 10^6$ | 8 |
|  | 19 | 100 mg/kg × once | Oral | 10 | b | $1.2 \times 10^6$ | 8 |
|  | 23 | 100 mg/kg × once | Oral | 10 | b | $1.2 \times 10^6$ | 8 |
|  | 24 | 100 mg/kg × once | Oral | 10 | b | $1.2 \times 10^6$ | 8 |
|  | 25 | 100 mg/kg × once | Oral | 10 | b | $7.7 \times 10^5$ | 8 |
|  | 26 | 100 mg/kg × once | Oral | 10 | b | $7.7 \times 10^5$ | 8 |
|  | Control | — | — | — | — | $1.2 \times 10^6$ | 8 |
| T-7-T | tropolone | 200 mg/kg × once | Oral | 20 | a | $1.9 \times 10^5$ | 5 |
|  | tropolone | 200 mg/kg × once | Oral | 20 | c | $1.9 \times 10^5$ | 5 |
|  | tylosin | 200 mg/kg × once | Oral | 20 | DW | $1.9 \times 10^5$ | 5 |
|  | doxycycline | 200 mg/kg × once | Oral | 20 | DW | $1.9 \times 10^5$ | 5 |
|  | Control | — | — | — | — | $1.9 \times 10^5$ | 5 |
|  | tropolone | 100 mg/kg × once | Oral | 10 | b | $10^2$ | 8 |
|  | 13 | 100 mg/kg × once | Oral | 10 | b | $10^2$ | 8 |
|  | 11 | 100 mg/kg × once | Oral | 10 | b | $10^2$ | 8 |
|  | 19 | 100 mg/kg × once | Oral | 10 | b | $10^2$ | 8 |
|  | 23 | 100 mg/kg × once | Oral | 10 | b | $10^2$ | 8 |
|  | 24 | 100 mg/kg × once | Oral | 10 | b | $10^2$ | 8 |
|  | tylosin | 100 mg/kg × once | Oral | 10 | b | $10^2$ | 8 |
|  | Control | — | — | — | — | $10^2$ | 8 |
| MR-1 | tropolone | 100 mg/kg × once | Oral | 10 | b | $0.3 \times 10^5$ | 6 |
|  | tylosin | 100 mg/kg × once | Oral | 10 | b | $0.3 \times 10^5$ | 6 |
|  | Control | — | — | — | — | $0.3 \times 10^5$ | 6 |

| Change of air-sac right | | | | Change of air-sac left | | | | Index of Disease | Myco-Isolated Chickens | Isolation T | L | R | Index of Isolation |
|---|---|---|---|---|---|---|---|---|---|---|---|---|---|
| − | + | ++ | +++ | − | + | ++ | +++ |  |  |  |  |  |  |
| 4 | 1 | 0 | 0 | 5 | 0 | 0 | 0 | 0.2 | 0 | ND | 0 | 0 | 0 |
| 3 | 2 | 0 | 0 | 5 | 0 | 0 | 0 | 0.4 | 2 | ND | 0 | 2 | 0.4 |
| 5 | 0 | 0 | 0 | 5 | 0 | 0 | 0 | 0 | 1 | ND | 0 | 1 | 0.2 |
| 4 | 1 | 0 | 0 | 5 | 0 | 0 | 0 | 0.2 | 1 | ND | 0 | 1 | 0.2 |
| 5 | 0 | 0 | 0 | 5 | 0 | 0 | 0 | 0 | 0 | ND | 0 | 0 | 0 |
| 0 | 1 | 0 | 4 | 5 | 0 | 0 | 0 | 2.6 | 5 | ND | 0 | 5 | 1.0 |
| 5 | 0 | 0 | 0 | 5 | 0 | 0 | 0 | 0 | 1 | 0 | 0 | 1 | 0.2 |
| 5 | 0 | 0 | 0 | 5 | 0 | 0 | 0 | 0 | 0 | 0 | 0 | 0 | 0 |
| 0 | 0 | 5 | 0 | 5 | 0 | 0 | 0 | 2.0 | 5 | 5 | 5 | 5 | 6.0 |
| 5 | 0 | 0 | 0 | 5 | 0 | 0 | 0 | 0 | 4 | 0 | 0 | 4 | 0.8 |
| 4 | 1 | 0 | 0 | 5 | 0 | 0 | 0 | 0.2 | 2 | 1 | 0 | 2 | 0.8 |
| 0 | 0 | 0 | 5 | 5 | 0 | 0 | 0 | 3.0 | 5 | 4 | 1 | 5 | 3.2 |

TABLE 2-continued

| | | | | | | | | | | | | | |
|---|---|---|---|---|---|---|---|---|---|---|---|---|---|
| 8 | 0 | 0 | 0 | 8 | 0 | 0 | 0 | 0 | 0 | 0 | 0 | 0 | 0 |
| 7 | 1 | 0 | 0 | 8 | 0 | 0 | 0 | 0.1 | 3 | 3 | 2 | 2 | 1.75 |
| 8 | 0 | 0 | 0 | 8 | 0 | 0 | 0 | 0 | 2 | 1 | 2 | 0 | 0.54 |
| 8 | 0 | 0 | 0 | 8 | 0 | 0 | 0 | 0 | 2 | 2 | 1 | 1 | 1.01 |
| 8 | 0 | 0 | 0 | 8 | 0 | 0 | 0 | 0 | 4 | 4 | 1 | 1 | 1.90 |
| 8 | 0 | 0 | 0 | 8 | 0 | 0 | 0 | 0 | 7 | 7 | 4 | 1 | 2.70 |
| 7 | 1 | 0 | 0 | 8 | 0 | 0 | 0 | 0.13 | 7 | 7 | 6 | 5 | 4.38 |
| 2 | 4 | 2 | 0 | 8 | 0 | 0 | 0 | 1.00 | 8 | 8 | 8 | 5 | 4.88 |
| 0 | 0 | 6 | 2 | 6 | 0 | 2 | 0 | 3.30 | 8 | 7 | 8 | 8 | 5.75 |
| 5 | 0 | 0 | 0 | 5 | 0 | 0 | 0 | 0 | 3 | 3 | 2 | 2 | 2.8 |
| 5 | 0 | 0 | 0 | 5 | 0 | 0 | 0 | 0 | 5 | 5 | 4 | 4 | 5.2 |
| 0 | 0 | 1 | 4 | 5 | 0 | 0 | 0 | 2.8 | 5 | 5 | 4 | 5 | 5.4 |
| 1 | 0 | 4 | 0 | 2 | 2 | 1 | 0 | 3.2 | 5 | 5 | 5 | 5 | 6.0 |
| 0 | 0 | 3 | 2 | 4 | 1 | 0 | 0 | 2.8 | 5 | 5 | 4 | 5 | 5.4 |
| 8 | 0 | 0 | 0 | 8 | 0 | 0 | 0 | 0 | 2 | 1 | 1 | 0 | 0.40 |
| 8 | 0 | 0 | 0 | 8 | 0 | 0 | 0 | 0 | 2 | 2 | 1 | 1 | 0.90 |
| 8 | 0 | 0 | 0 | 8 | 0 | 0 | 0 | 0 | 5 | 5 | 1 | 4 | 2.90 |
| 8 | 0 | 0 | 0 | 8 | 0 | 0 | 0 | 0 | 5 | 5 | 2 | 1 | 2.00 |
| 8 | 0 | 0 | 0 | 8 | 0 | 0 | 0 | 0 | 6 | 6 | 6 | 5 | 4.20 |
| 8 | 0 | 0 | 0 | 8 | 0 | 0 | 0 | 0 | 5 | 5 | 3 | 3 | 2.80 |
| 1 | 1 | 5 | 1 | 6 | 0 | 2 | 0 | 2.80 | 8 | 8 | 8 | 7 | 5.60 |
| 0 | 0 | 0 | 8 | 7 | 0 | 1 | 0 | 3.50 | 8 | 8 | 3 | 8 | 6.00 |
| 6 | 0 | 0 | 0 | 6 | 0 | 0 | 0 | 0 | 6 | 3 | 3 | 4 | 3.2 |
| 0 | 0 | 3 | 3 | 5 | 1 | 0 | 0 | 2.8 | 6 | 6 | 6 | 6 | 6.0 |
| 0 | 0 | 0 | 6 | 3 | 3 | 0 | 0 | 4.0 | 6 | 6 | 5 | 4 | 5.2 |

*Amount of tropolone-derivatives is shown as that calculated for tropolone molecule.
Conc: concentration, Sol.: Solution, T: trachea, R: right and L: left (3) Acute toxicity test Acute toxicity tests on tropolone L-lysine salt and O-acetyltropolone were performed according to the following method.

The tests had been done on 15 days old SPF chickens of layer type (5 males and 5 females) for 2 weeks. The above two compounds suspended in 5% gum arabic are orally and forcibly administered once at a dose of 400 mg/kg or 200 mg/kg. To a control group is administered 5% gum arabic.

The result showed that in terms with the increase of weight the group of O-acetyltropolone-administration was a little inferior to the control-group and the group of tropolone L-lysine salt-administration was equal to the control group. In both of administration groups none of chickens died.

What we claim is:

1. A method for the treatment of an animal infected by mycoplasma which comprises orally administering to said animal a composition which comprises o-acetyltropolone or a pharmaceutically acceptable salt thereof as the active ingredient dissolved in feed water or mixed with a feed in a concentration of 100 to 1000 parts of the compound or salt thereof per million parts of feed water or feed.

* * * * *